United States Patent [19]

Gardiner et al.

[11] 4,341,469

[45] Jul. 27, 1982

[54] LASER SHADOWGRAPH

[75] Inventors: Mark E. Gardiner, Westwood; David W. Kuntz, Pacific Palisades, both of Calif.

[73] Assignee: Discovision Associates, Costa Mesa, Calif.

[21] Appl. No.: 160,611

[22] Filed: Jun. 18, 1980

[51] Int. Cl.³ ............................................. G01N 21/41
[52] U.S. Cl. ..................................... 356/239; 356/391
[58] Field of Search ............... 356/239, 391, 392, 393, 356/354

[56] References Cited

U.S. PATENT DOCUMENTS 2,958,255 11/1960 Dietrich ............................... 356/391
3,964,830 6/1976 Ikeda et al. .......................... 356/239
4,030,835 6/1977 Firester et al. ....................... 356/354

FOREIGN PATENT DOCUMENTS 2258702 6/1973 Fed. Rep. of Germany ...... 356/239

Primary Examiner—Vincent P. McGraw
Attorney, Agent, or Firm—Ronald J. Clark

[57] ABSTRACT

Apparatus for producing a shadowgraph image of a transparent part to be examined, such as part of a video disc. The apparatus includes a source of coherent light, and an objective lens system for focusing the coherent light to produce a divergent beam, a concave mirror disposed in the path of the divergent beam, a transparent plate for supporting the disc to be examined in the aperture of the concave mirror, and a projection screen to receive light reflected from the concave mirror. The apparatus may also include plane mirrors to permit the projection screen to be positioned in a convenient location with respect to the disc being examined.

5 Claims, 7 Drawing Figures

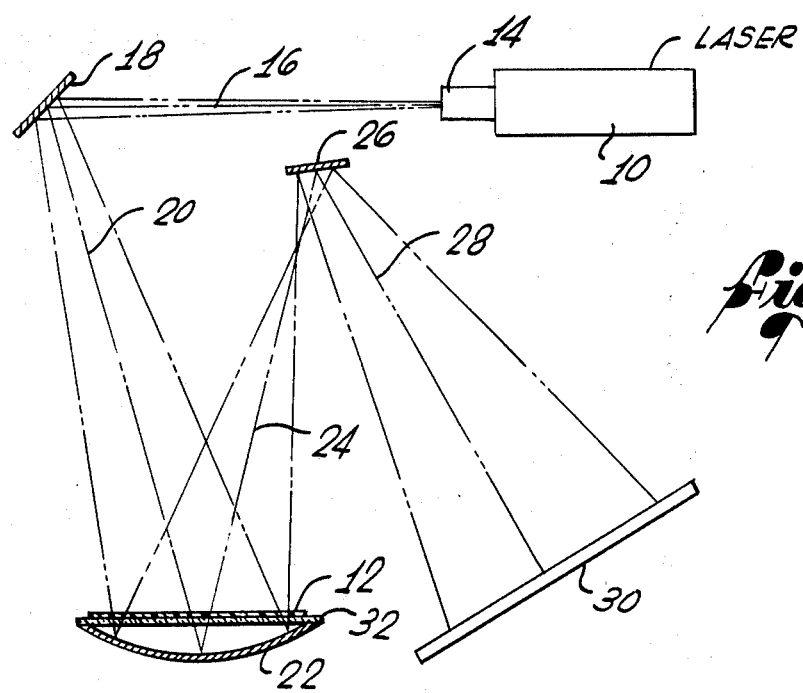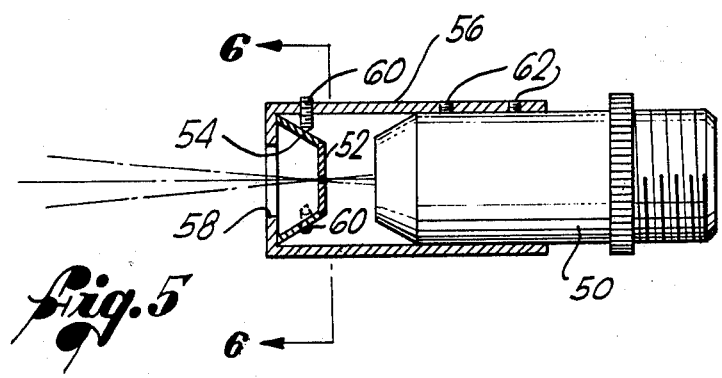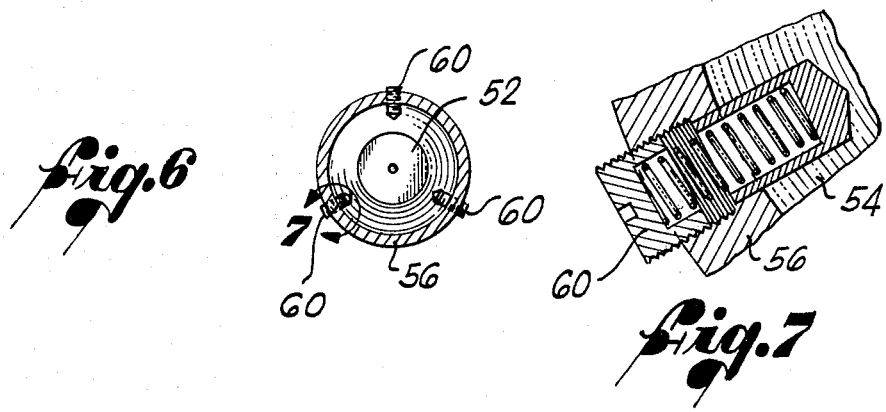

LASER SHADOWGRAPH

BACKGROUND OF THE INVENTION

This invention relates generally to shadowgraph imaging apparatus, and, more particularly, to shadowgraph apparatus for detecting defects in recording disks. In general terms, a shadowgraph is an optical image formed by shadows cast on a screen when a source of radiation is directed onto the screen through an object being examined. In this broad sense, x-ray pictures are shadowgraphs. Shadowgraphs are also employed to study the characteristics of fluid flow around objects such as aircraft, ballistic devices, and so forth. Light passing through the moving fluid is used to produce a shadow image caused by refraction through density gradients in the fluid. This technique is commonly referred to as the schlieren method.

In video disc recording technology, video information is recorded on a master disc, from which a great many copies are subsequently made for sale to the general public. Typically, the disc copies are formed in a plastics molding machine. In one process, each face of a finished disk is formed separately as a transparent disc-shaped element, then the two separate elements are bonded together and further processed to form the finished disc. Reproduction of information from the disk may be effected optically, using a laser beam, or may require the use of a transducer that senses changes in some electrical characteristic. In any event, the information is carried on the disc in the form of surface discontinuities that can be detected optically or electrically. Apart from these discontinuities, the surface must be completely clear of optical aberrations that could effect the quality of the reproduced signal. In the past, disc inspection has been carried out by viewing the transparent disc element against a white light source. Although this technique is satisfactory for detecting serious defects in the discs, small anomalies undetectable to the human eye can still create significant problems when the recorded information is played back from the disc.

Accordingly, since the introduction of video disc recording systems, requiring the production of discs to a high degree of accuracy, there has been a significant need for a quality control technique to ensure that manufactured discs are free of anomalies that could affect the quality of reproduction. The present invention is directed to this end.

SUMMARY OF THE INVENTION

The present invention resides in a shadow-graph device for use in the detection of defects in transparent discs, such as video recording discs, for purposes of controlling the quality of the discs and for adjusting operating parameters of the process used for form the disc. Briefly, and in general terms, the apparatus of the invention comprises a source of coherent light, focusing means for producing a divergent beam from the light source, a concave mirror disposed in the path of the divergent beam, means for supporting a disc to be examined within the aperture of the concave mirror, and a projection screen positioned in the path of light reflected from the mirror. In the presently preferred embodiment of the invention, the disc to be examined and the projection screen on which its shadowgraph image is projected are oriented substantially horizontally and are disposed side by side in the apparatus. To accomplish this end, the concave mirror is disposed horizontally, i.e., with its optical axis vertical and its concave surface uppermost, and the invention apparatus further includes two plane mirrors, one to reflect the divergent beam from the light source down into the concave mirror, and the other disposed to reflect light from the concave mirror back down onto the projection screen. The means for supporting the disc is preferably a flat sheet of optical quality glass or other transparent material. Small defects in the surface of the disc show up conspicuously in the shadowgraph image, typically in the form of a series of concentric interference rings.

In accordance with one aspect of the invention, the focusing means includes a microscope objective lens and a pinhole aperture. The aperture must be adjustable both radially and axially to coincide with the focal point of the beam emerging from the objective lens, and in accordance with this aspect of the invention, radial and axial adjustments are effected by means of simple set screws, rather than by cumbersome and expensive micrometer mechanisms.

It will be appreciated from the foregoing that the prevent invention represents a significant advance in the field of manufacture of optical quality discs, such as video recording discs. In particular, the use of a laser light source in conjunction with an objective lens system, concave mirror and projection screen, allow the detection of extremely small flaws in the disc. Other aspects and advantages of the invention will become apparent from the following more detailed description, taken in conjunction with the accompanying drawings.

BRIEF DESCRIPTION OF THE DRAWINGS

FIG. 1 is a simplified schematic view showing the arrangement of optical components in the apparatus of the invention;

FIG. 5 is an enlarged view, partly in section, of an objective lens system used in the apparatus of FIGS. 2-4;

FIG. 6 is a sectional view taken substantially among the lines 6—6 of FIG. 5; and FIG. 7 is a further enlarged view of the portion shown within the circle 7 in FIG. 6.

DETAILED DESCRIPTION

Figure 2:
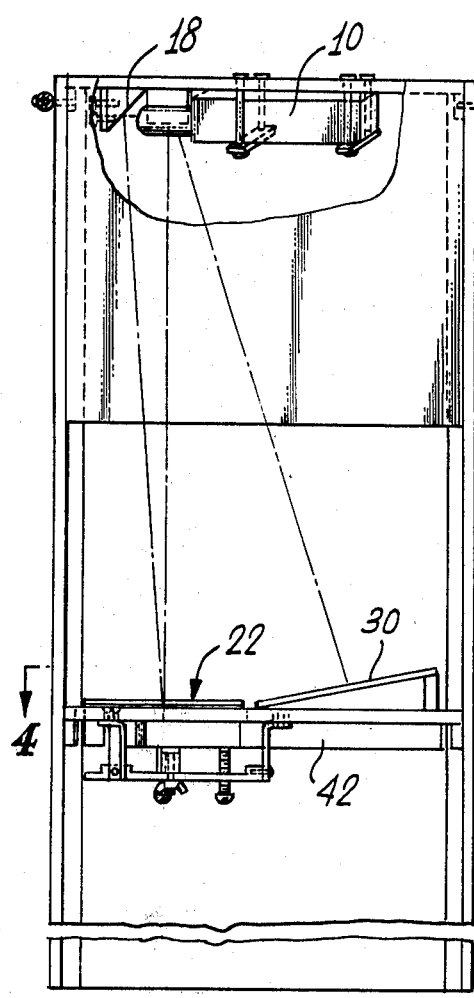
FIG. 2 is an elevational view of a presently preferred embodiment of the apparatus.

As shown in the drawings for purposes of illustration, the present invention is principally concerned with optical apparatus for the shadowgraph display of a transparent part, such as a video disc.

In accordance with the invention, a laser light source, indicated by reference numeral 10, provides a beam of coherent light for the examination of a transparent disc 12. The light from the laser 10 is focused by an objective lens system 14, from which the light emerges as a divergent beam, the centerline of which is indicated at 16. The beam 16 impinges upon a first plane mirror 18, and is reflected along a path shown by centerline 20 to a concave mirror 22. The divergent light beam practically fills the aperture of the concave mirror 22 and is reflected as indicated by the beam centerline 24 to a second plane mirror 26, which again reflects the beam along centerline 28 to a projection screen 30. The disc 12 being examined is supported on a plane glass sheet 32 in the aperture of the concave mirror 22. In the preferred embodiment of the invention, the disc 12 and the screen 30 are disposed practically side by side in an approximately horizontal configuration. Accordingly, in this embodiment, the beam 16 from the laser 10 is substantially horizontal and the first mirror 18 reflects the incident beam through almost ninety degrees, to a direction inclined only slightly from the vertical. The beam reflected along path 24 from the concave mirror is also practically vertical, and the second mirror 26 reflects this beam back down to the screen 30.

By examination of the shadowgraph image obtained in this manner, defects in discs can be readily detected. The apparatus can be used both as a quality control tool and to provide data for adjustment of molding machines used to produce the discs.

Figure 3:
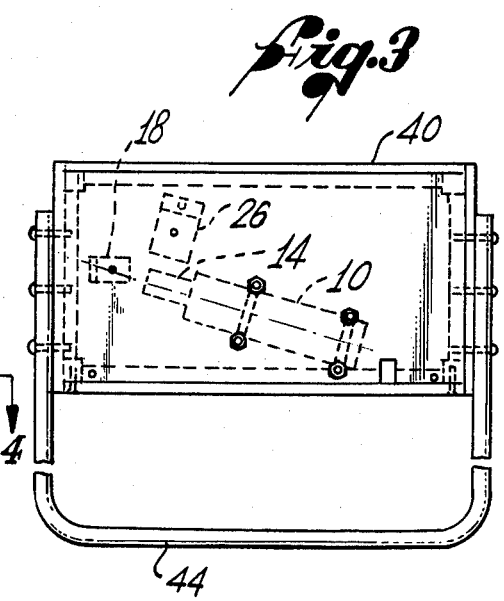
FIG. 3 is a plan view of the apparatus shown in FIG. 2.
Figure 4:
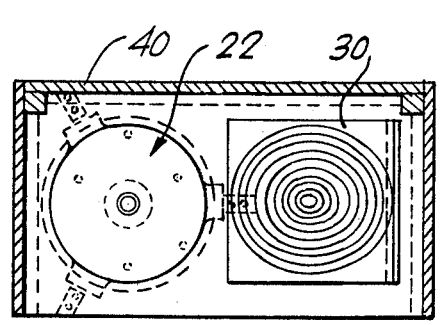
FIG. 4 is a sectional view taken substantially along the line 4—4 in FIG. 2.

FIGS. 2–4 show the shadowgraph device of the invention in more mechanical detail. The components are housed in an open-front cabinet 40 of approximately the same size as a telephone booth. It will be seen that the laser 10 is secured to the top of the cabinet 40, as is the first plane mirror 18. The laser utilized in the illustrative embodiment is a 5-milliwatt (mW) He-Ne laser. Light reflected from the mirror 18 is directed practically vertically to the concave mirror 22, and is reflected by the concave mirror back to the top region of the cabinet, where the second plane mirror 26 is located adjacent to the laser 10. The mirror 26 reflects the light beam back toward the bottom of the cabinet where it impinges on the screen 30 and produces the desired shadowgraph. The concave mirror 22 and the screen 30 are both supported on a shelf 42 fixed inside the cabinet 40 at a convenient height for a standing or sitting operator. A curtain rail 44 is provided to support a black-out curtain employed to obtain better viewing conditions.

In the embodiment shown, the concave mirror 22 is a telescope mirror of 12.5 inch (31.75 cm) diameter and a focal length of 23 inches (58.4 cm). The glass sheet 32 used to support the disc 12 is also 12.5 inches (31.75 cm) in diameter.

The objective lens system system 14 of the invention includes a microscope objective lens, such as an Olympus M40X objective, indicated by reference numeral 50 in FIGS. 5–7, a bi-concave lens (not shown) of $-20$ mm focal length, and a 50 micron pinhole aperture or spatial filter, indicated by reference numeral 52. The pinhole aperture is supported at the focal point of the objective lens 50, and is affixed to a generally conical aperture mount 54. The aperture mount is, in turn, secured inside a cylindrical sleeve 56 sized to slide over the cylindrical body of the objective lens 50. The sleeve 56 is completely open at one end, to slide over the objective lens 50, and has a relatively large aperture 58 at the other end. The conical aperture mount 54 is disposed in the sleeve 56 with its larger diameter end abutting the apertured end of the sleeve, and with its smaller-diameter end supporting the pinhole aperture 52.

In accordance with one aspect of the invention, the pinhole aperture 52 can be centered by means of three set-screws 60, and is adjustable axially by means of set-screws 62. The three set screws 60 are disposed through threaded openings in the sleeve 56 and engage the conical walls of the pinhole aperture mount 54. When appropriately tightened, the set-screws 60 tend to bias the mount 54 and the pinhole aperture 52 towards the apertured end of the sleeve 56. By appropriate adjustment of the three set-screws 60, one of which is spring-loaded as shown in detail in FIG. 7, the pinhole aperture 52 can be moved to a limited extent in a plane perpendicular to the light beam. Loosening of the set screws 62, which clamp the sleeve 56 onto the objective lens 50, allows axial adjustment of the entire assembly including the sleeve 56 and the aperture 52.

It will be appreciated from the foregoing that the present invention represents a significant advance in the field of optical inspection of transparent parts, such as video discs. In particular, the use of coherent light in the specific optical arrangement described allows the detection of much smaller optical defects, at easily observable irradiance levels on the projection screen, than was previously possible. It will also be appreciated that, although a specific embodiment of the invention has been described in detail for purposes of illustration, various modifications may be made without departing from the spirit and scope of the invention. Accordingly, the invention is not to be limited except as by the appended claims.

We claim:

1. Shadowgraph apparatus for the inspection of transparent discs, said apparatus comprising:
    a source of coherent light;
    focusing means for producing a divergent beam from said light source;
    a concave mirror disposed in the path of the divergent beam for producing a converging beam by reflecting said diverging beam;
    means for supporting a disc to be examined within the aperture of said concave mirror; and
    a projection screen positioned in the path of light reflected from said concave mirror beyond the convergence point thereof, whereby a shadowgraph image of the disc to be examined is formed on said projection screen.

2. Shadowgraph apparatus as set forth in claim 1 wherein:
    said means for supporting a disc and said projection screen are oriented approximately horizontally and side-by-side; and
    said apparatus further includes a first plane mirror positioned to reflect the divergent beam from said source of coherent light approximately vertically onto said concave mirror, and a second plane mirror positioned to reflect light received from said concave mirror back to said projection screen.

3. Shadowgraph apparatus as set forth in claim 1, wherein said focusing means includes:
    a microscope-type objective lens assembly for focusing the light from said source to a focal point;
    a pinhole aperture positionable at the focal point;
    an aperture mount to which the aperture is affixed;
    a sleeve securable to said objective lens assembly and containing said aperture and aperture mount;
    a plurality of set-screws disposed radially through said sleeve, to bear on said aperture mount, whereby adjustment of said set-screws permits centering of said pinhole aperture; and
    at least one additional set-screw disposed radially through said sleeve and bearing on said objective lens assembly, to permit axial adjustment of said pinhole aperture.

4. Shadowgraph apparatus for the inspection of transparent video recording discs, said apparatus comprising:
    a laser light source;

focusing means for producing a divergent beam from said laser light source;

a first plane mirror positioned to reflect the divergent beam to a substantially vertical direction;

a concave mirror positioned to receive the divergent beam from said first plane mirror and to produce a converging beam by reflecting said diverging beam;

a flat transparent plate positioned over the aperture of said concave mirror, for supporting a disc to be inspected;

a second plane mirror positioned to receive light reflected from said concave mirror and to reflect it back to a position adjacent to said concave mirror; and an opaque projection screen positioned adjacent to said concave mirror to receive light from said second plane mirror beyond the convergence point of said light and to display a shadowgraph image of the disc to be inspected.

5. Shadow graph apparatus as set forth in claim 4, wherein said focusing means includes:

a microscope-type objective lens assembly for focusing the light from said source to a focal point;

a pinhole aperture positionable at the focal point;

an aperture mount to which the aperture is affixed;

a sleeve securable to said objective lens assembly and containing said aperture and aperture mount;

a plurality of set-screws disposed radially through said sleeve, to bear on said aperture mount, whereby adjustment of said set-screws permits centering of said pinhole aperture; and at least one additional set-screw disposed radially through said sleeve and bearing on said objective lens assembly, to permit axial adjustment of said pinhole aperture.

* * * * *